United States Patent
Gagel et al.

(10) Patent No.: US 11,504,459 B2
(45) Date of Patent: Nov. 22, 2022

(54) DIALYSATE CONCENTRATION MEASUREMENT SENSOR DIAGNOSIS

(71) Applicant: FRESENIUS MEDICAL CARE DEUTSCHLAND GMBH, Bad Homburg (DE)

(72) Inventors: Alfred Gagel, LItzendorf (DE); Tilman Staeblein, Wuerzburg (DE)

(73) Assignee: FRESENTUS MEDICAL CARE DEUTSCHLAND GMBH, Bad Homburg (DE)

( * ) Notice: Subject to any disclaimer, the term of this patent is extended or adjusted under 35 U.S.C. 154(b) by 556 days.

(21) Appl. No.: 16/476,440

(22) PCT Filed: Jan. 3, 2018

(86) PCT No.: PCT/EP2018/050104
§ 371 (c)(1),
(2) Date: Jul. 8, 2019

(87) PCT Pub. No.: WO2018/134045
PCT Pub. Date: Jul. 26, 2018

(65) Prior Publication Data
US 2020/0054808 A1   Feb. 20, 2020

(30) Foreign Application Priority Data
Jan. 20, 2017 (DE) ..................... 10 2017 000 495.1

(51) Int. Cl.
*A61M 1/16*   (2006.01)
*A61M 1/14*   (2006.01)
*G06F 1/00*   (2006.01)
*G06F 1/16*   (2006.01)

(52) U.S. Cl.
CPC ............ *A61M 1/1656* (2013.01); *A61M 1/14* (2013.01); *G06F 1/00* (2013.01); *G06F 1/16* (2013.01); *A61M 2205/3317* (2013.01); *A61M 2205/70* (2013.01)

(58) Field of Classification Search
CPC .................. A61M 1/14; A61M 1/1656; A61M 2205/3317; A61M 2205/70; G06F 1/00; G06F 1/16
See application file for complete search history.

(56) References Cited

U.S. PATENT DOCUMENTS

2005/0045540 A1   3/2005   Connell et al.
2010/0192686 A1*  8/2010   Kamen ............... A61M 1/1601
                                                  73/290 R

FOREIGN PATENT DOCUMENTS

| EP | 2767296 | 8/2014 |
| EP | 3254712 A1 * | 12/2017 |
| JP | 2013-081662 | 5/2013 |
| WO | WO 2016/125902 | 8/2016 |

* cited by examiner

Primary Examiner — John Kim
(74) Attorney, Agent, or Firm — Jacobson Holman PLLC

(57) ABSTRACT

A diagnosis method for a conductivity sensor for a dialysis fluid preparation apparatus and personal dialysis apparatus, that mix water, an A fluid and a B fluid in predetermined proportions respectively to prepare a dialysis fluid and measures the concentration of the prepared dialysis fluid by concentration measurement means is described. The diagnosis method and the respective apparatus is based in measuring the A fluid without the B fluid being present in the solution.

14 Claims, 3 Drawing Sheets

DIALYSATE CONCENTRATION MEASUREMENT SENSOR DIAGNOSIS

TECHNICAL FIELD

Figure 1:
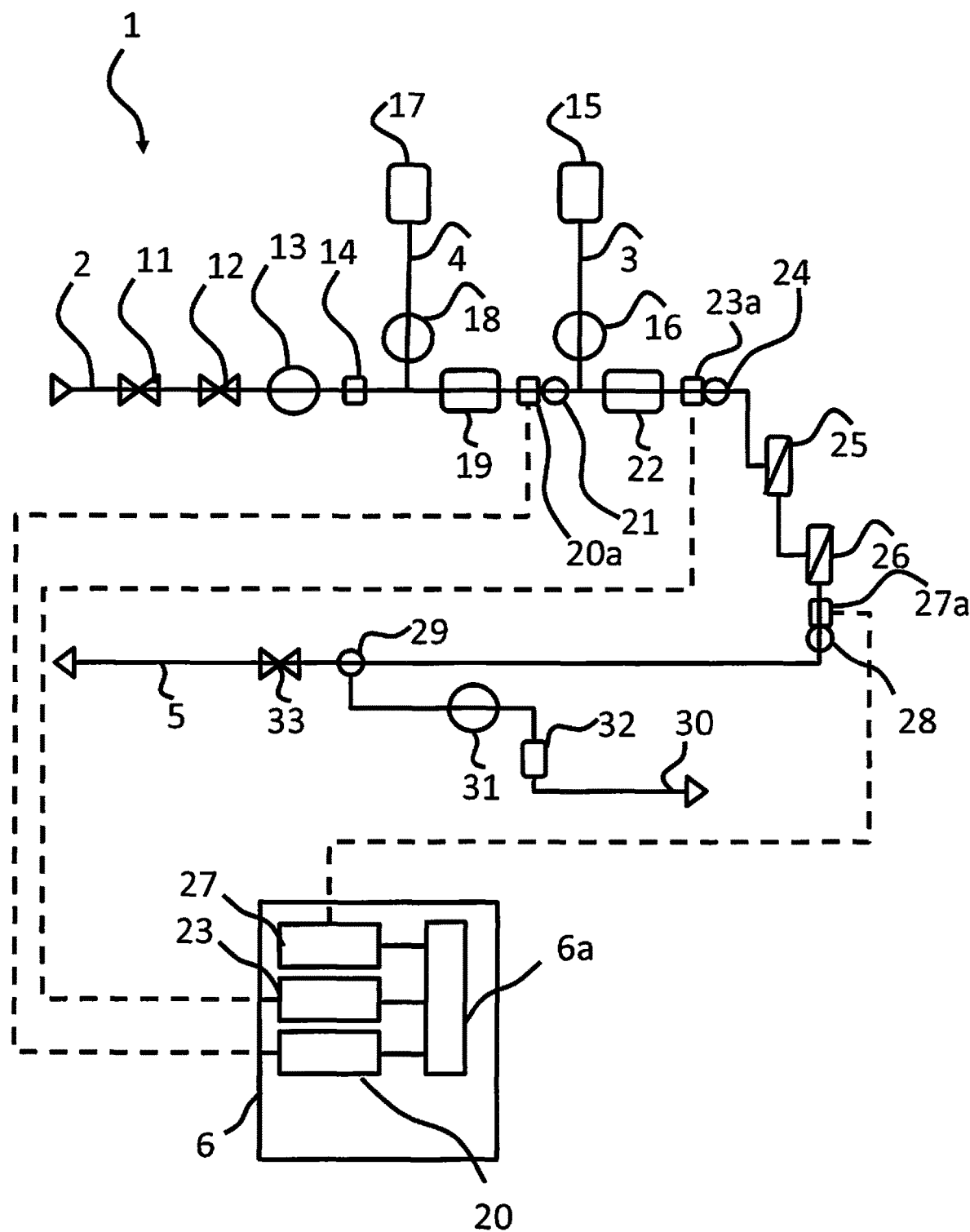

The present invention relates to a diagnosis method for a dialysis fluid preparation apparatus and personal dialysis apparatus, that mix water, an A fluid and a B fluid in predetermined proportions respectively to prepare a dialysis fluid and measure the concentration of the prepared dialysis fluid by concentration measurement means.

BACKGROUND

Conventionally, a dialysis fluid preparation apparatus is known to include a water feed passage that feeds water, an A fluid passage that is connected with the water feed passage and feeds an A fluid containing sodium chloride as a principal ingredient, and a B fluid passage that is connected with the water feed passage and feeds a B fluid composed of a sodium bicarbonate aqueous solution, in order to prepare a dialysis fluid to be used in a dialysis apparatus.

Such a dialysis fluid preparation apparatus includes concentration measurement means provided with a detection unit for electric conductivity measurement downstream of the connecting positions of the A fluid passage and the B fluid passage on the water feed passage, in order to judge whether the prepared dialysis fluid corresponds to the expected composition.

EP 2767296 A1 describes a dialysis fluid preparation apparatus, a personal dialysis apparatus, and a method to assess the accuracy of a conductivity sensor by feeding the sodium bicarbonate aqueous solution concentrate to the water feed passage and measuring the conductivity value by comparing it with a previously set value.

SUMMARY OF THE INVENTION

Problem to be Solved

EP 2767296 A1 describes the benefit of using the bicarbonate solution for the diagnosis as it has always the same concentration whereas the other fluids to be mixed with the bicarbonate fluid to generate the dialysis fluid may vary in its concentrations.

However, the inventors have recognized that this only applies under special circumstances and, therefore, intended to develop a method and a device that allows to assess the accuracy of a conductivity sensor more independently from the system in use and broadly applicable.

When preparing the devices for hemodialysis or any variant thereof, such as hemodiafiltration, high-volume hemodiafiltration, or any other chronic or acute extracorporeal blood treatments using a dialysate, the A and the B concentrates may be provided as solutions, for example in canisters, or as dry concentrates, for example in flexible bags or formstable cartridges, to which water is fed to generate a liquid concentrate that is the dosed to the water feed passage to generate a dialysate.

If ready-made solutions are used, both concentrates are normally completely dissolved and the concentration of the dissolved ions and, therefore, the conductivity is known prior to setting-up the machine.

This situation is different in case that the concentrates are provided as dry concentrates. For the B concentrate, consisting of a single salt which is normally sodium bicarbonate a saturated solution is generated, maintaining solid sodium bicarbonate in the container where the solution is generated.

However, the solubility of bicarbonate salts are temperature dependent and, therefore, the temperature of the solution needs to be known to judge the projected conductivity of the solution for diagnosing the conductivity sensor accuracy.

Therefore, additional effort is needed to determine the projected conductivity of a saturated bicarbonate solution, which is in particular the provision of a temperature sensor to the measure the temperature in the container and processing means to calculate the conductivity for the measured temperature.

It is the objective to provide a conductivity sensor diagnosis method and device to overcome the above identified problem.

Means for Solving the Problems

The above-identified problems are solved by a method and a device of the independent claims. The dependent claims describe embodiments of the method and device of the independent claims.

The inventors have recognized that the A concentrate normally comprises at least two different ingredients, for example salts and, therefore, the concentrate must be provided in use in a completely dissolved manner to ensure that the concentration and in particular the relative concentration of the ingredients in the solution is determined. This means the concentration, in particular the relative concentration does not change if more or less liquid is in the container containing the ingredients of the A concentrate and independent of the temperature. This applies for both cases, provision as a solution or provision as a dry concentrate that is to be dissolved at the machine.

The diagnosis method may be applied to a dialysis fluid preparation apparatus having a water feed passage to feed water, an A fluid passage to feed an A fluid containing sodium chloride as a principal ingredient together with at least one other ingredient, the A fluid passage being connected with the water feed passage, a B fluid passage to feed a B fluid composed of a sodium bicarbonate aqueous solution, the B fluid passage being connected with the water feed passage, and concentration measurement means provided with a detection unit downstream of connecting positions of the A fluid passage and the B fluid passage on the water feed passage. The diagnosis method may comprise mixing the water, the A fluid and the B fluid in predetermined proportions respectively to prepare a dialysis fluid, and measuring a concentration of the prepared dialysis fluid by the concentration measurement means, and before preparing the dialysis fluid, feeding the A fluid from the A fluid passage to the water feed passage so as to flow only the A fluid to the water feed passage, and diagnosing an accuracy of the concentration measurement means by measuring an electric conductivity of the A fluid, undiluted or diluted, by the concentration measurement means and comparing the measured electric conductivity of the A fluid or of the diluted A fluid respectively with a previously set value.

The diagnosis method may be performed on the A fluid in an undiluted or in a diluted form. This means, either only A fluid is sent to the concentration measurement means or the A fluid is diluted with a known amount of water, for example from the water feed passage. In both cases the previously set value is a conductivity value that is expected for the respective composition of the A fluid in diluted or undiluted form. If this measured conductivity, however, is not measured, it is an indication that one of the components of the concentration measurement means does not function properly.

The diagnosis method for the dialysis fluid preparation apparatus may comprise, when measuring the electric conductivity of the A fluid, measuring a time after an A fluid pump starts a fluid sending of the A fluid and before the concentration measurement means measures a concentration of the A fluid, the A fluid pump being provided on the A fluid passage and feeding the A fluid to the water feed passage, and thereby diagnosing fluid sending accuracy of the A fluid pump.

This test allows excluding one potential error, which is a malfunction of the A fluid pump, that may lead to a deviation of the measured electric conductivity from the previous set value and, therefore, allows increasing the probability that the deviation originates from a malfunction of the sensor of the concentration measurement means.

To generate the diluted A fluid, the diagnosis method for the dialysis fluid preparation apparatus may mix the water and the A fluid to prepare a preparation fluid of the A fluid by flowing the water to the water feed passage.

The diagnosis method for the dialysis fluid preparation apparatus may further comprise displaying on a display of the dialysis fluid preparation apparatus a message that the user shall check if an A fluid type used as an input parameter for determining the previously set value corresponds to an A fluid type of the A fluid. This message may be displayed based on the result of the comparison of the measured electric conductivity of the A fluid or of the diluted A fluid with the previously set value, in particular if a deviation between the measured electric conductivity and the previously set value exceeds a predetermined threshold value.

This test allows excluding one further potential error, which is a mismatch between the A fluid which is connected to the dialysis fluid preparation apparatus and the set value in the machine, that may lead to a deviation of the measured electric conductivity from the previous set value and, therefore, allows increasing the probability that the deviation originates from a malfunction of the sensor of the concentration measurement means.

The diagnosis method for the dialysis fluid preparation apparatus may further comprise displaying on the display of the dialysis fluid preparation apparatus an error message indicating malfunction of the dialysis fluid preparation apparatus if an A fluid type used as input parameter for determining the previously set value corresponds to an A fluid type of the A fluid. This message may be displayed based on the result of the comparison of the measured electric conductivity of the A fluid or of the diluted A fluid with a previously set value, in particular if a deviation between the measured electric conductivity and the previously set value exceeds a predetermined threshold value.

The diagnosis method for the dialysis fluid preparation apparatus may comprise providing a user interaction means, which may be a touch screen or an operation panel or a button or any other known type of user interaction device, to confirm that the A fluid type used as the input parameter for determining the previously set value corresponds to the A fluid type of the A fluid, and displaying on the display of the dialysis fluid preparation apparatus a warning message, for example that the user shall inform the service if the user interaction means has been activated by the user. This interaction means may be activation button that is displayed only based on the result of the comparison of the measured electric conductivity of the A fluid or of the diluted A fluid with a previously set value, in particular if a deviation between the measured electric conductivity and the previously set value exceeds a predetermined threshold value.

The diagnosis method for the dialysis fluid preparation apparatus may comprise that the previously set value is a value based on a further electric conductivity measured by a further detection means of a further concentration measurement means positioned in the A fluid passage or the water feed passage downstream to the connection of the A fluid passage to the water feed passage.

By identifying the previously set value in this way, it is possible to be independent from the entry by the operator or any other data transfer. Further, as the same liquid is passing both concentration measurement means sensors the probability of an error based on pumping errors may be reduced.

A dialysis fluid preparation apparatus according to the invention comprises a water feed passage to flow water, a water feed pump provided on the water feed passage, an A fluid passage to feed an A fluid containing sodium chloride as a principal ingredient together with at least one other ingredient, the A fluid passage being connected with the water feed passage, an A fluid pump provided on the A fluid passage, a B fluid passage to feed a B fluid composed of a sodium bicarbonate aqueous solution, the B fluid passage being connected with the water feed passage, a B fluid pump provided on the B fluid passage, concentration measurement means provided with a detection unit downstream of connecting positions of the A fluid passage and the B fluid passage on the water feed passage, and control means to control actuations of the pumps. The control means of the dialysis fluid preparation apparatus is configured to control mixing the water, the A fluid and the B fluid in predetermined proportions to prepare a dialysis fluid. Further, the control means is provided with a diagnosis unit to diagnose accuracy of the concentration measurement means by actuating the A fluid pump to perform a fluid sending of only the A fluid to the water feed passage, in particular without performing a fluid sending with the B fluid pump, wherein the diagnosis unit is configured to diagnose the accuracy of the concentration measurement means by comparing an electric conductivity of the A fluid, undiluted or diluted, measured by the detection unit of the concentration measurement means with a previously set value.

The dialysis fluid preparation apparatus may further be configured to, when measuring the electric conductivity of the A fluid, measuring a time after the A fluid pump starts sending of the A fluid and before the concentration measurement means measures the concentration of the A fluid, and thereby to diagnose a fluid sending accuracy of the B fluid pump.

The dialysis fluid preparation apparatus may further may be configured, to generate the diluted A fluid, to mix the water and the A fluid to prepare a preparation fluid of the A fluid by flowing the water to the water feed passage.

The dialysis fluid preparation apparatus may further comprise a display. The display may be a screen, a touch screen, a signaling light or any other device to provide information to a user.

The dialysis fluid preparation apparatus may further may be configured to display on the display a message that the user shall check if an A fluid type used as an input parameter for determining the previously set value corresponds to an A fluid type of the A fluid. This message may be displayed based on the result of the comparison of the measured electric conductivity of the A fluid or of the diluted A fluid with a previously set value, in particular if a deviation between the measured electric conductivity and the previously set value exceeds a predetermined threshold value.

The dialysis fluid preparation apparatus may further may be configured to display on the display on the display an error message indicating malfunction of the dialysis fluid preparation apparatus if an A fluid type used as input parameter for determining the previously set value corresponds to an A fluid type of the A fluid. This message may be displayed based on the result of the comparison of the measured electric conductivity of the A fluid or of the diluted A fluid with a previously set value, in particular if a deviation between the measured electric conductivity and the previously set value exceeds a predetermined threshold value.

The dialysis fluid preparation apparatus may further may comprise a user interaction means.

The dialysis fluid preparation apparatus may be configured, upon activation of the user interaction means confirming that the A fluid type used as the input parameter for determining the previously set value corresponds to the A fluid type of the A fluid, to display on the display of the dialysis fluid preparation an error message indicating malfunction of the dialysis fluid preparation.

The dialysis fluid preparation apparatus may further may comprise a further detection means of a further concentration measurement means positioned in the A fluid passage or the water feed passage downstream to the connection of the A fluid passage to the water feed passage. The dialysis fluid preparation apparatus may further may be configured to use as previously set value a value based on a further electric conductivity measured by the further detection means.

In all of the embodiments herein, the use of the expression "may be" or "may have" and so on is intended to illustrate an exemplary embodiment according to the present invention. Embodiments according to the present invention may comprise one or several of the aforementioned or following features. Thereby the features mentioned herein may in any arbitrary combination be subject-matter of embodiments according to the present invention, unless the person skilled in the art recognizes their combination as technically impossible. Embodiments according to the present invention are subject-matter of the dependent claims as well. Whenever numerical words are mentioned herein, the person skilled in the art shall recognize or understand them as indications of numerical lower limits. Unless it leads the person skilled in the art to an evident contradiction, the person skilled in the art shall comprehend the specification for example of "one" is encompassing "at least one". This understanding is also equally encompassed by the present invention as the interpretation that a numeric ward, for example, "one" may alternatively mean "exactly one", wherever this is evidently technically possible for the person skilled in the art. Both are encompassed by the present invention and apply herein to all used numerical words.

Embodiments of the dialysis fluid preparation method and the dialysis fluid preparation apparatus will be described referring to the figures.

Figure 2:
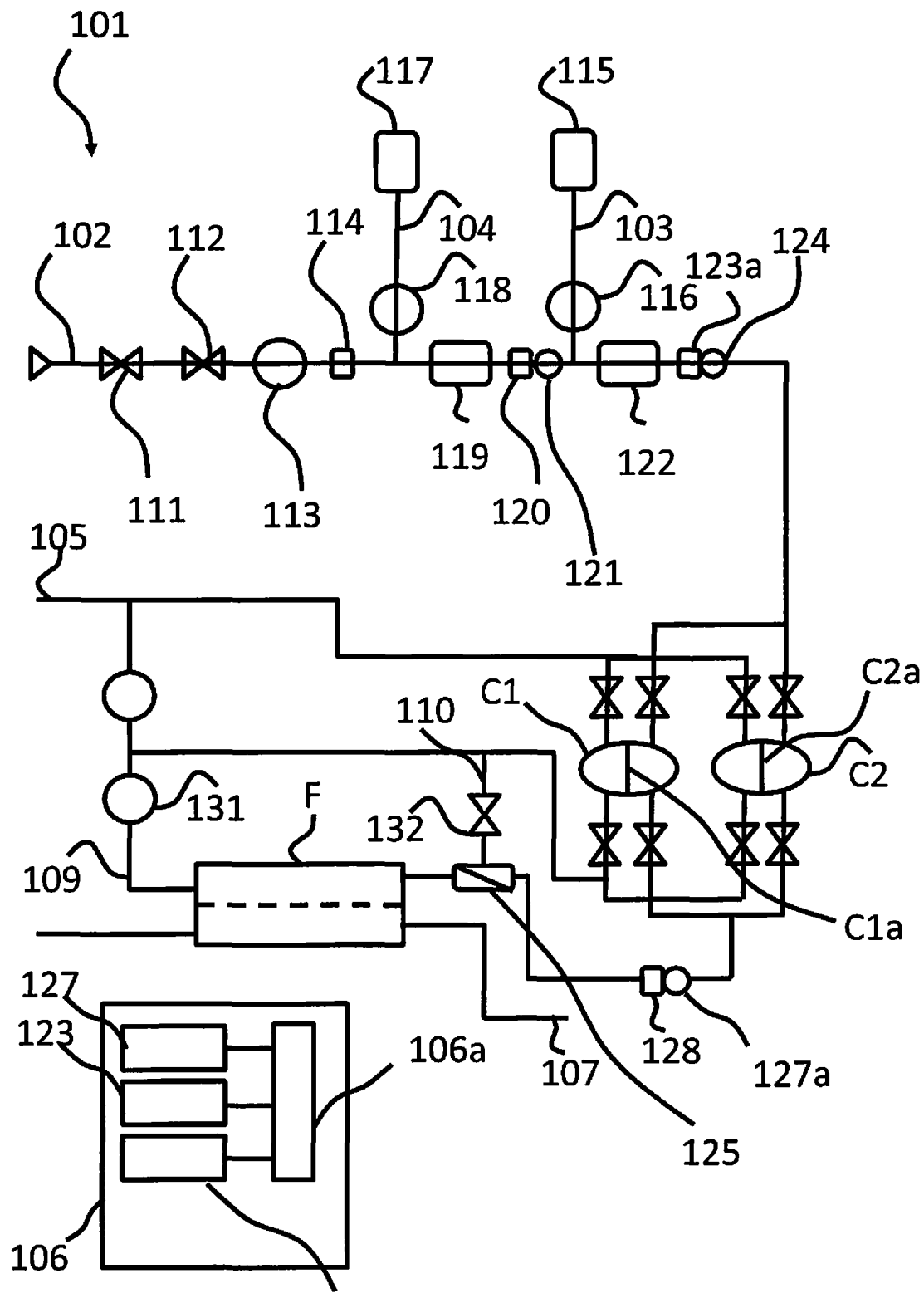
Figure 3:
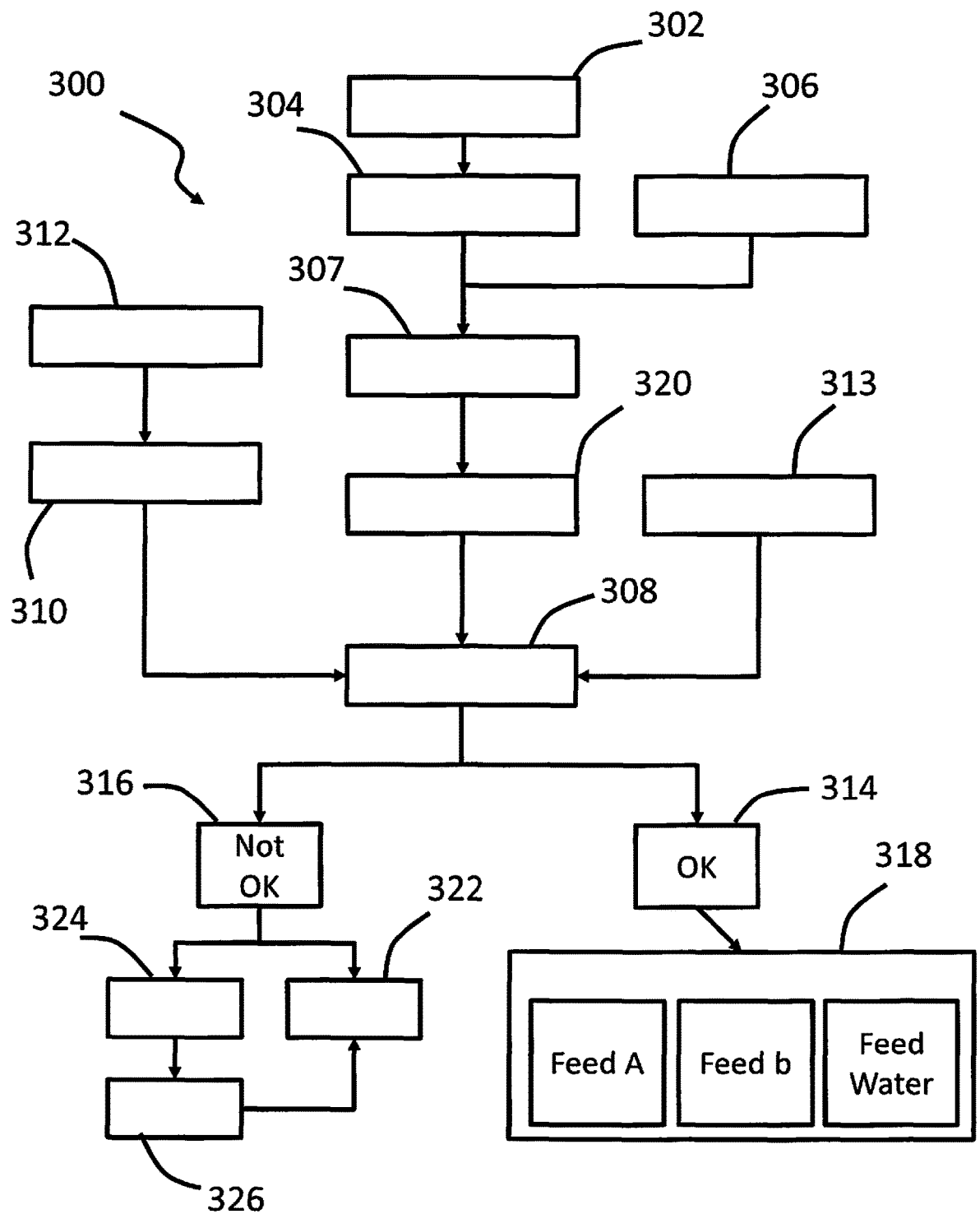

FIG. 1 shows a schematic configuration diagram of a dialysis fluid preparation apparatus according to a first embodiment, FIG. 2 shows a schematic configuration diagram of a personal dialysis apparatus according to a second embodiment, and FIG. 3 shows a schematic flow diagram of the diagnosis according to an embodiment of the invention.

Hereinafter, embodiments shown in the drawings will be described. FIG. 1 shows a dialysis fluid preparation apparatus 1 that may be installed in hospitals and the like. This dialysis fluid preparation apparatus 1 may feed a prepared dialysis fluid to a plurality of dialysis monitoring apparatuses not shown in the figure, as a so-called dialysis fluid feed apparatus for many persons.

FIG. 2, which shows a second embodiment, illustrates a configuration diagram of a so-called personal dialysis apparatus 101. This personal dialysis apparatus 101 comprises also a function as the diagnosis fluid preparation apparatus 1 shown in FIG. 1, and can prepare the diagnosis fluid. Therefore, dialysis fluid preparation apparatus 1 as described below may be integral part of the personal dialysis apparatus 101.

Correspondingly, the embodiments of dialysis fluid preparation apparatus 1 as described below are also embodiments of the personal dialysis apparatus 101 when integrated in the personal dialysis apparatus 101.

To outline the similarities the respective elements in the dialysis fluid preparation apparatus 1 and the personal dialysis apparatus 101 have the following reference numbers:

1: dialysis fluid preparation apparatus—101: personal dialysis apparatus
  2: water feed passage—102
  3: A fluid passage—103
  4: B fluid passage—104
  5: waste fluid passage—105
  6: control means—106
  6a: diagnosis unit—106a
  12: adjusting valve—112
  13: water pump—113
  14: flow meter—114
  15: A fluid tank—115
  16: A fluid pump—116
  17: B fluid tank—117
  18: B fluid pump—118
  19: First buffer tank—119
  20: first concentration measurement means—120
  20a: first detection unit—120a
  21: temperature sensor—121
  22: Second buffer tank—122
  23: second concentration measurement means—123
  23a: second detection unit—123a
  24: temperature sensor—124
  25: first filter—125
  26: second filter
  27: third concentration measurement means—127
  27a: third detection unit—127a
  28: temperature sensor—128
  29: connection port
  30: Fluid Feed Passage—108
  31. Fluid sending pump—C in combination with 131
  32: Drip Chamber
  On-off valve 132
  33: On-off valve The dialysis fluid preparation apparatus 1 includes a water feed passage 2 that is connected with water feed means to feed water, which is not shown in the FIG. 1. A fluid passage 3 that is connected with the water feed passage 2 and feeds an A fluid as an undiluted fluid ingredient of the dialysis fluid, a B fluid passage 4 that is connected with the water feed passage 2 and feeds a B fluid. The dialysis fluid preparation apparatus may further comprise a waste fluid passage 5 that is led from the water feed passage 2 and drains a poor dialysis fluid. One or more pumps 13, 18, 16 of the dialysis fluid preparation apparatus 1 may be controlled by a control means 6 (respective control lines are not shown). Actuation of solenoid on-off valves may also be controlled by the control means 6. The water may be fed through the water feed passage 2. If the dialysis preparation device 1 is part of a personal-dialysis device 101 the water feed passage 2 or the water feed passage 102, accordingly, may be guided through further elements of the dialysis fluid preparation apparatus 1 such as a degassing chamber, a heating chamber, air separation chamber (elements not shown).

"Undiluted" has the meaning of having a higher concentration of at least one ingredient than in the dialysis solution used during treatment. Basically, "undiluted" means the material in the containers 15, 17 in comparison to that material if mixed with water from the water feed passage 2.

The water feed passage 2 may be connected at the inlet side to water purification means for generating purified water (not shown). The water purification means may be an RO water generator. The RO water generator may include a deionizing means to provide water with very low and/or stable and/or predetermined electric conductivity.

The A fluid as an undiluted fluid of the dialysis fluid is comprises sodium chloride as an ingredient, and other than sodium chloride, also contains at least one other ingredient. The other ingredient may be at least one or more or all materials of the group comprising magnesium chloride, calcium chloride, potassium chloride, citric acid, glucose, dextrose. The ratio may be different depending on the patient for which its use is intended, and therefore, the concentration of the A fluid itself may vary for the dialysis fluid to be prepared.

On the other hand, the B fluid as an undiluted fluid component of the dialysis fluid is composed of an aqueous solution containing only sodium bicarbonate.

As described in detail later, the dialysis fluid preparation apparatus 1 has a self-check function to previously diagnose the device comprising the dialysis fluid preparation apparatus 1 before preparing the dialysis fluid, and can switch between a diagnosis mode for performing the self-check and a preparation mode for performing the preparation of the dialysis fluid.

The B fluid passage 4 may be connected upstream of the A fluid passage 3 on the water feed passage 2. Upstream of the connecting position of the B fluid passage 4, a first on-off valve 11 to open and close the water feed passage 2, a water pump 13 to send the water may be provided. Further, an adjusting valve 12 to adjust the flow rate of the purified water in the water feed passage 2 and/or a flow meter 14 to measure the flow rate of the water may be provided on the upstream side of the connection point of the B fluid passage 4 and/or the A fluid passage 3 to the water feed passage 2.

The adjusting valve 12, which may be a needle valve, may be configured to adjust the flow rate of the water that the water pump 13 sends, by the control of the control means 6. Alternatively or in addition, the control means may control the flow rate of the water by adjusting the pump speed of pump 13. In this case the adjusting valve 12 may be omitted. The flow meter 14 may measure the flow rate, and feeds back for the flow rate adjustment of the adjusting valve 12. The A fluid passage 3 has one end connected with an A fluid tank 15 in which the A fluid is pooled, and an A fluid pump 16 to send the A fluid is provided on the A fluid passage 3. Similarly to this, the B fluid passage 4 is connected with a B fluid tank 17 in which the B fluid is pooled, and a B fluid pump 18 to send the B fluid is provided on the B fluid passage 4.

The A fluid tank 15 and/or the B fluid tank 17 may be a formstable cartridges or flexible bags. Solid ingredients of the A fluid and/or the B-Fluid may be provided in the tank 15, 17 in a solid phase, for example as powders, granules or a mixture thereof, and the dialysis fluid preparation apparatus 1 may comprise a fluid connection from the water feed passage 2 to feed water to at least one or both of the A fluid tank 15 and the B fluid tank 17. Thus, the undiluted fluids of the A fluid and the B fluid may be generated after the solid material containing containers 17, 15 have been attached to the dialysis fluid preparation apparatus 1. It is understood that also slurries or other constitutions between solid and complete solutions may be used.

The A fluid pump 16 and the B fluid pump 18 may be volume pumps respectively, and include motors not shown in the figures. By running these motors at predetermined rotation speeds, it is possible to feed the A fluid and the B fluid to the water feed passage 2 at predetermined flow rates set in the control means 6.

Between the B fluid passage 4 and the A fluid passage 3 on the water feed passage 2 at least one of a first buffer tank 19 for temporarily pooling liquid, a detection unit 20a of a first concentration measurement means 20 to measure the concentration of the liquid, and a first temperature measurement means 21 to measure the temperature of the liquid may be provided.

Downstream of the A fluid passage 3 on the water feed passage 2 a detection unit 23a of a second concentration measurement means 23 to measure the concentration of the liquid is provided. Further, downstream of the A fluid passage 3 at least one or more of the following elements may be provided: a second buffer tank 22 for temporarily pooling liquid, a second temperature measurement means 24 to measure the temperature of the liquid, a first filter 25 to purify the dialysis fluid, a detection unit 27a of a third concentration measurement means 27 to measure the concentration of the liquid, and a third temperature measurement means 28 to measure the temperature of the liquid. Preferably, the temperature sensors 21, 24, 28 are located in the close vicinity of the detections units 20a, 23a, 27a as the output of the concentration measurement means may be temperature compensated base on the output of the temperature measurement means. This may allow for a more appropriate comparison result of the measured electrical conductivity and the previously set value.

A second filter 26 to purify the dialysis fluid may be provided downstream to the first filter 25.

The dialysis fluid path as an extension of the water flow path 2, in which upon operation the dialysate generated in the dialysis fluid preparation apparatus 1 flows, may be connected to a the waste fluid passage 5 via connection port 29. The connection port 29 may be positioned downstream to at least one of the above identified detections units 20a, 23a, 27a. An on-off valve 33 may be provided on the waste fluid passage 5 after the connection port 29.

For a stand-alone embodiment of the dialysis fluid preparation apparatus 1, further a fluid sending pump 31 to send the dialysis fluid and a drip chamber 32 may be provided on a fluid feed passage 30 connected to the dialysis fluid path. By activating this pump, the dialysate may be provided to one or more dialysis monitor apparatus. The fluid drip chamber 32 may also be not present.

For an embodiment of the personal dialysis apparatus 101, a fluid sending pump being for example comprising a balancing system including balancing chambers C1, C2 and pump 131 may be provided to send the dialysis fluid to the dialyzer F, wherein the balancing system may be provided upstream to the filter 125. The type of balancing chamber system is not restricted to a balancing chamber system. Alternatively, the personal dialysis apparatus 101 may have a feed pump and waste pump and the balancing is conducted by controlling the flows generated by the two pumps.

The first and second buffer tanks 19, 22 form spaces in which the diameter of a part of the water feed passage 2 is enlarged and liquid is mixed, mixing may take place by stirring. In the first buffer tank 19, the B fluid and the purified water are mixed so that a preparation fluid of the B fluid is prepared. In the second buffer tank 22, the A fluid is mixed with the preparation fluid of the B fluid so that the dialysis fluid is prepared.

The ratio between the B fluid and the water in the preparation fluid of the B may be identical to the ratio between the B fluid and the water in the dialysis fluid that is prepared by the dialysis fluid preparation apparatus 1. The concentration of the B fluid may be measured, and may be registered in the control means 6. The same applies for the A fluid.

Also, as for the dialysis fluid the concentration may be previously measured, and may be registered in the control means 6. As for this concentration, multiple kinds are registered depending on the A fluid to be used. Also further conductivities for different A fluids and B fluids and different mixing ratios may be registered. Registration includes also providing an algorithm for calculating the electric conductivity based on the component and their ratio, for example water, A fluid, and B fluid, wherein the registration may also include the calculation methods where the ingredients for A fluid types and also B fluid types with their concentrations are pre-stored in the dialysate preparation device 1 or the personal-dialysis apparatus 101.

If present the first and second filters 25, 26 may remove endotoxins in the prepared dialysis fluid. The endotoxins are surely removed by the two filters.

The first to third concentration measurement means 20, 23, 27 are concentration meters that convert the electric conductivities of the liquids, which are respectively measured by the first to third detection units 20a, 23a, 27a including electrodes, into the concentrations of the liquids, and are incorporated in the control means 6. However, when using the expression "concentration measuring means" the step to determine from the electric conductivity a concentration is an optional step to determine the concentration. It is sufficient to assess the conductivity value itself.

The first to third temperature measurement means 21, 24, 28 are disposed adjacent to the first to third detection units 20a, 23a, 27a, respectively, and the first to third concentration measurement means 20, 23, 27 may correct the converted concentration values by the measured liquid temperatures.

When the dialysis fluid preparation apparatus 1 is in the dialysis fluid preparation mode, the first concentration measurement means 20 may measure the electric conductivity of the preparation fluid of the B fluid, potentially prepared in the first buffer tank 19 if present, and the second and third concentration measurement means 23, 27 may measure the electric conductivity of the dialysis fluid prepared, potentially prepared in the second buffer tank 22 if present.

The control means 6 may compare these electric conductivities of the preparation fluid of the B fluid and the dialysis fluid that are measured by the first to third concentration measurement means 20, 23, 27, with the previously registered electric conductivities of the preparation fluid of the B fluid and the dialysis fluid, and judges whether these electric conductivities are abnormal.

The dialysis fluid preparation apparatus 1 may further be configured to run in a diagnosis mode for performing a self-check. This diagnosis mode may be timewise positioned before preparing the dialysis fluid. The diagnosis mode may be part of an initial test phase in which various functionalities of the device, in particular of the personal dialysis apparatus 101.

Thereby, the control means 6 may include a diagnosis unit 6a for performing the self-check, and, in this diagnosis unit 6a, diagnoses the accuracy of at least one of the first to third concentration measurement means 20, 23, 27.

It is noted that for this invention in general if the expressions "accuracy" or "precision" is used this also includes a basic functionality test. It does not require that the accuracy of precision is quantified.

FIG. 2, which shows a second embodiment, illustrates a configuration diagram of the so-called personal dialysis apparatus 101. As outlined already above this personal dialysis apparatus 101 has also a function as the diagnosis fluid preparation apparatus 1 shown in FIG. 1 and described by referring to FIG. 1, and can prepare the diagnosis fluid.

In the following embodiment, as for common constituents with the above first embodiment, reference numerals resulting from adding 100 to the reference numerals used in the first embodiment are used, and detailed descriptions are omitted.

The personal dialysis apparatus 101 may include or may be configured to include, for example by provision of respective connections ports for the dialysis fluid, a dialyzer F to perform the dialysis between blood and dialysis fluid, a blood circuit 107 to be connected between the dialyzer F and a patient, and the first and second chambers C1, C2 to feed fresh dialysis fluid to the dialyzer F and retrieve used dialysis fluid. The first and second chambers C1, C2 may respectively be divided into feed chambers in which the fresh dialysis fluid is pooled by diaphragms C1a, C2a having flexibility, and retrieval chambers in which the used dialysis fluid is pooled. The feed chambers may be connected with a water feed passage 102 and a fluid feed passage 108 that feeds the fresh dialysis fluid to the dialyzer F, and the retrieval chambers may be connected with a waste fluid passage 105 and a retrieval passage 109 that retrieves the used diagnosis fluid from the dialyzer F. On these passages, various solenoid on-off valves may be provided respectively.

The water feed passage 2 in the first embodiment corresponds to the water feed passage 102 and fluid feed passage 108 in the second embodiment, and the detection unit 127a of the third concentration measurement means 127, the third temperature measurement means 128 and the first filter 125 may each be provided on the fluid feed passage 108. The third concentration measurement means 127 and the third temperature measurement means 128 may be provided upstream of the first filter 125 on the fluid feed passage 108, and the second filter 26 in the first embodiment may be omitted. Further, the fluid sending pump 131 may be provided on the retrieval passage 109.

A bypass passage 110 may be formed between the first filter 125 and the retrieval passage 109, and by opening a second on-off valve 132 provided on the bypass passage 110, the dialysis fluid judged as a poor concentration may be drained.

The personal dialysis apparatus 101 having the above described configuration, itself, is known conventionally, and therefore, detailed descriptions of the behavior are omitted. Similarly to the above first embodiment, the personal dialysis apparatus 101 can diagnose the accuracy of the first to third concentration measurement means 120, 123, 127 with a diagnosis unit 106a provided in a control means 106, and can also diagnose the fluid sending rate of a B fluid pump 118 and an A fluid pump 116.

In a further embodiment, the B fluid passage may be connected downstream of the A fluid passage, and it is possible to diagnose the accuracy of the first to third concentration measurement means 120, 123, 127 in this in comparison to the in FIG. 2 shown embodiment reversed connection.

Hereinafter, the behavior of the dialysis fluid preparation apparatus 1 having the above configuration will be described. A diagnosis method 300 for diagnosing the accuracy of at least one of the first to third concentration measurement means 20, 23, 27 will be described. This is schematically shown in FIG. 3. By referring to FIG. 3 also other steps of the method are described, but as it is clear from the description some of the steps are optional. As outlined above the description based on the features of the embodiments described by referring to the dialysis fluid preparation apparatus 1 are also embodiments of the personal dialysis apparatus 101.

Initially, the A fluid passage 3 and the B fluid passage 4 are connected with the A fluid tank 15 and the B fluid tank 17 in which the A fluid and B fluid to be used in the preparation of the dialysis fluid are provided, respectively, and the water feed passage 2 is connected to a water source. In this state, an operator may operate 302 a user interaction means not shown in the figure to initiate the diagnosis mode to actuate the self-check function and the diagnosis unit 6*a* of the control means 6 diagnoses the accuracy of the concentration measurement means. As described above further checks for example of each of the solenoid on-off valves, pumps and measurement means, and therewith may be initiated.

At step 304 the A fluid pump 16 on the A fluid passage 3 is actuated. At this time, the B fluid pump 18 is being stopped. Optionally, in parallel water may be fed 306 by actuating the water feed pump 13 to generate a diluted solution of the A fluid.

Thereby, the A fluid, which is fed from the A fluid tank 15, flows into the water feed passage 2 through the A fluid passage 3, and the water, having previously been filled in the water feed passage 2 is pushed to the waste fluid passage 5. Eventually, the water feed passage 2 becomes a state in which the downstream side of the connecting position of the A fluid passage 3 is filled with only the A fluid or diluted A fluid.

When, after the actuation of the A fluid pump 16, enough time has elapsed for the A fluid to come to at least one of the detection units 20*a*, 23*a*, 27*a* of the second and third concentration measurement means 20, 23, 27, the control means 6 may measure, step 307, the electric conductivity with at least one the second to third detection units 20*a*, 23*a*, 27*a* of the second to third concentration measurement means 20, 23, 27.

Then at step 308, the diagnosis unit 6*a* compares the measured electric conductivity with a previously set value. The previously set value may be a value that is stored in a memory 310. The previously set value may have been identified based on an input 312 of an operator identifying the A fluid type, wherein the A fluid type allows for identifying its ingredients, an automatic identification of the A fluid type or any other means. This may take place based on a database provided in the memory 310. Other parameters to determine the previously set value may be the dosing ratio between the A fluid and the water if diluted A fluid is to be measured. The respective information may be provided to a processor, for example the diagnosis unit 6*a* or another processor in the apparatus. Alternatively, or in addition the previously set value may be a value measured 313 with one of detection units 20*a*, 23*a*, 27*a* of the second and third concentration measurement means 20, 23, 27 different from the concentration measurement means 20,23, 27 to be diagnosed.

If the measured value of the A fluid, undiluted or diluted, measured at this time is in a predetermined error range for the previously set value, a diagnosis as being not abnormal is made 314 in the diagnosis unit 6*a*, and if leaving the error range, a diagnosis as being abnormal is made 316.

If the diagnosed one of the concentration measurement means 20, 23, 27 being abnormal, the control means 6 may give a warning 322 for the appropriate concentration measurement means. The warning 322 may be an information to inform the service. If the at least one or all diagnosed concentration measurement means 20, 23, 27 is not abnormal, the control means 6 may proceed with an operation described below.

The diagnosis method may further comprise displaying 324 on the display, if a deviation between the measured electric conductivity and the previously set value exceeds a predetermined threshold value, a message that the user shall check if the A fluid type used as an input parameter for determining the previously set value corresponds to the A fluid type of the A fluid, and upon activation of a user interaction means confirming 326 that the A fluid type used as the input parameter for determining the previously set value corresponds to the A fluid type of the A fluid, displaying 322 on the display of the dialysis fluid preparation an error message indicating malfunction of the dialysis fluid preparation.

If it has been determined 314 that there is no abnormal state for the at least one diagnosed concentration measurement means 20, 23, 27, the dialysis fluid preparation apparatus 1 may proceed and enter in a dialysis fluid preparation mode or a treatment mode 318 including mixing A fluid, B fluid and water to prepare the dialysis fluid.

Additionally or alternatively the control means 6 may continuously measure the electric conductivity with at least one of the detection units 20*a*, 23*a*, 27*a*. After the A fluid pump 16 starts to send the A fluid, and the control means 6 may measure the time before the electric conductivity reaches the above predetermined value, that is, the time before the A fluid reaches the respective detection unit 20*a*, 23*a*, 27*a*. Then, the diagnosis unit 6*a* may compare the measured reaching time of the A fluid with a previously set standard time, and judges whether the A fluid pump 16 is abnormal 320. If the reaching time is later than the standard time, the fluid sending rate of the A fluid pump 16 is insufficient, and if being earlier, the fluid sending rate is greater than the specification.

In case that the measuring of the electric conductivity was measuring of the A fluid only with the respective detection units 20*a*, 23*a*, 27*a* of the first to third concentration measurement means 20, 23, 27, the control means 6 may open the first on-off valve 11 on the water feed passage 2, and may further actuate the water pump 13 to flow the water to the water feed passage 2 at a predetermined flow rate.

On this occasion, the A fluid pump 16 may perform the fluid sending at a specified flow rate, and thereby, in the second buffer tank 22, if present, on the water feed passage 2, the A fluid and the water are mixed so that the preparation fluid of the A fluid is prepared at a predetermined concentration. This preparation fluid of the A fluid may flow to the waste fluid passage 5.

Similarly to the case of sending only the A fluid, the control means 6 measures the electric conductivity with at least one of the first to third detection units 20*a*, 23*a*, 27*a*, and the diagnosis unit 6a compares the measured values with a previously set value corresponding to the concentration of the preparation fluid of the A fluid.

By measuring the concentrations of the A fluid and the preparation fluid of the A fluid, that is, the liquids with different electric conductivities, in this way, it is possible to diagnose the first to third concentration measurement means 20, 23, 27 more exactly.

This second measurement on the diluted A fluid corresponds to the above described process of diagnosing via the diluted A fluid and may, therefore, be conducted alone or in combination with the diagnosis method using the pure A fluid.

After measuring the electric conductivity of the preparation fluid of the A fluid with the detection units 20a, 23a, 27a of the first to third concentration measurement means 20, 23, 27 in this way, the control means 6 may actuate the A fluid pump 16 on the A fluid passage 3 to feed the A fluid to the water feed passage 2, and further may actuate the B fluid pump 18, and thereby, in the second buffer tank 22, if present, positioned downstream of the connecting position of the A fluid passage 3, the B fluid is mixed to the preparation fluid of the A fluid so that the dialysis fluid is prepared. The dialysis fluid may flow in the water feed passage 2 to the waste fluid passage 5.

The control means 6 may measure the electric conductivity of the dialysis fluid with the second detection unit 23a of the second concentration measurement means 23 and the third detection unit 27a of the third concentration measurement means 27, compares it with a previously set value as the electric conductivity of the dialysis fluid, and judges whether the concentration of the dialysis fluid is good or poor.

Further, by measuring the time after the B fluid pump 18 may start to feed the B fluid and before the second detection unit 23a may measure the electric conductivity corresponding to the predetermined concentration of the dialysis fluid, it is possible to diagnose the fluid sending rate of the B fluid pump 16.

Thus, the diagnosis of the accuracy of the first to third concentration measurement means 20, 23, 27 is completed, and when the other devices also are not recognized to be abnormal, the control means 6 finishes the diagnosis of the dialysis fluid preparation apparatus 1. The dialysis fluid preparation apparatus 1 switches from the diagnosis mode to the preparation mode, and subsequently prepares 318 the dialysis fluid. This switch may also be initiated by an operator.

Thus, in the dialysis fluid preparation apparatus 1 according to the above embodiment, by the diagnosis unit 6a provided in the control means 6, it is possible to automatically diagnose the accuracy of at least one of the first to third concentration measurement means 20, 23, 27.

Although, in the above embodiment, the B fluid passage 4 is connected upstream of the A fluid passage 3 on the water feed passage 2, it can be connected downstream of the A fluid passage 3. That is, it is possible to be configured such that, in FIG. 1, reference numeral 3 denotes the B fluid passage, reference numeral 4 denotes the A fluid passage, reference numerals 15, 16 denote the B fluid tank and the B fluid pump respectively, and reference numerals 17, 18 denote the A fluid tank and the A fluid pump respectively.

All embodiments may have more than one concentration measuring means with the respective detection unit. It shall be emphasized that the personal dialysis apparatus may have exactly one concentration measuring means with the respective detection unit upstream to the dialyzer. For the personal dialysis apparatus this is beneficial as it further reduced costs of the machine.

The invention claimed is:

1. A diagnosis method for a dialysis fluid preparation apparatus that comprises:
   a water feed passage to feed water,
   an A fluid passage to feed an A fluid and connected with the water feed passage,
   an A fluid tank containing the A fluid and connected with the A fluid passage, wherein the A fluid contains completely dissolved sodium chloride as a principal ingredient together with at least one other completely dissolved ingredient,
   a B fluid passage to feed a B fluid composed of a saturated sodium bicarbonate aqueous solution, the B fluid passage being connected with the water feed passage,
   a B fluid tank containing the B fluid and solid sodium bicarbonate and connected with the B fluid passage, and
   concentration measurement means provided with a detection unit downstream of connecting positions of the A fluid passage on the water feed passage,
   the diagnosis method comprising mixing the water, the A fluid and the B fluid in predetermined proportions respectively to prepare a dialysis fluid, and
   measuring a concentration of the prepared dialysis fluid by the concentration measurement means, characterized in that
   before preparing the dialysis fluid, feeding the A fluid from the A fluid passage to the water feed passage so as to flow only the A fluid to the water feed passage, and diagnosing an accuracy of the concentration measurement means by measuring an electric conductivity of the A fluid, undiluted or diluted, by the concentration measurement means and then comparing the measured electric conductivity of the A fluid with a previously set value.

2. The diagnosis method for the dialysis fluid preparation apparatus according to claim 1 further comprising:
   measuring a time after an A fluid pump starts a fluid sending of the A fluid and before the concentration measurement means measures a concentration of the A fluid, the A fluid pump being provided on the A fluid passage and feeding the A fluid to the water feed passage, and thereby diagnosing fluid sending accuracy of the A fluid pump.

3. The diagnosis method for the dialysis fluid preparation apparatus according to claim 1 further comprising:
   to generate the diluted A fluid, mixing the water and the A fluid to prepare a preparation fluid of the A fluid by flowing the water to the water feed passage.

4. The diagnosis method for the dialysis fluid preparation apparatus according to claim 1 further comprising:
   displaying on a display of the dialysis fluid preparation apparatus, if a deviation between of the measured electric conductivity and of the previously set value exceeds a predetermined threshold value, a message that a user shall check if an A fluid type used as an input parameter for determining the previously set value corresponds to an A fluid type of the A fluid connected to the A fluid passage.

5. The diagnosis method for the dialysis fluid preparation apparatus according to claim 4, further comprising:
   displaying on the display of the dialysis fluid preparation apparatus, an error message indicating malfunction of the dialysis fluid preparation apparatus, if an A fluid type used as the input parameter for determining the previously set value corresponds to the A fluid type of the A fluid connected to the A fluid passage.

6. The diagnosis method for the dialysis fluid preparation apparatus according to claim 5, further comprising:
providing a user interaction means, to confirm) that the A fluid type used as the input parameter for determining the previously set value corresponds to the A fluid type of the A fluid connected to the A fluid passage, and displaying on the display of the dialysis fluid preparation apparatus the error message if the user interaction means has been activated by the user.

7. The diagnosis method for the dialysis fluid preparation apparatus according to claim 1, further comprising that the previously set value is a value based on a further electric conductivity measured by a further detection means of a further concentration measurement means positioned in the A fluid passage or the water feed passage downstream to the connection of the A fluid passage to the water feed passage.

8. A dialysis fluid preparation apparatus comprising:
a water feed passage to flow water,
a water feed pump provided on the water feed passage,
an A fluid passage to feed an A fluid and connected with the water feed passage,
an A fluid pump provided on the A fluid passage,
an A fluid tank, for containing the A fluid, connected with the A fluid passage, wherein the A fluid contains completely dissolved sodium chloride as a principal ingredient together with at least one other completely dissolved ingredient,
a B fluid passage to feed a B fluid composed of a saturated sodium bicarbonate aqueous solution, the B fluid passage being connected with the water feed passage, a B fluid pump provided on the B fluid passage,
a B fluid tank, for containing the B fluid and solid sodium bicarbonate, connected with the B fluid passage,
concentration measurement means provided with a detection unit downstream of connecting positions of the A fluid passage on the water feed passage, and
control means to control actuations of the pumps,
wherein the control means of the dialysis fluid preparation apparatus is configured to control mixing the water, the A fluid and the B fluid in predetermined proportions to prepare a dialysis fluid, and wherein the control means is provided with a diagnosis unit, characterized in that the diagnosis unit is configured to diagnose accuracy of the concentration measurement means by actuating the A fluid pump to perform a fluid sending of only the A fluid to the water feed passage, without performing a fluid sending with the B fluid pump, wherein the diagnosis unit is configured to diagnose the accuracy of the concentration measurement means by comparing an electric conductivity of the A fluid, undiluted or diluted, measured by the detection unit of the concentration measurement means with a previously set value.

9. The dialysis fluid preparation apparatus according to claim 8, further configured to,
measure a time after the A fluid pump starts sending of the A fluid and before the concentration measurement means measures the concentration of the A fluid, and thereby to diagnose a fluid sending accuracy of the A fluid pump.

10. The dialysis fluid preparation apparatus according to claim 8, further configured to,
to generate the diluted A fluid, mix the water and the A fluid to prepare a preparation fluid of the A fluid by flowing the water to the water feed passage.

11. The dialysis fluid preparation apparatus according to claim 8, comprising a display, and
further being configured to display on the display, if a deviation between the measured electric conductivity and the previously set value exceeds a predetermined threshold value, a message that a user shall check if an A fluid type used as an input parameter for determining the previously set value corresponds to an A fluid type of the A fluid connected to the A fluid passage.

12. The dialysis fluid preparation apparatus according to claim 11, further being configured to display on the display an error message indicating malfunction of the dialysis fluid preparation apparatus if an A fluid type used as the input parameter for determining the previously set value corresponds to an A fluid type of the A fluid connected to the A fluid passage.

13. The dialysis fluid preparation apparatus according to claim 12, comprising a user interaction means, and
further being configured upon activation of the user interaction means confirming that the A fluid type used as the input parameter for determining the previously set value corresponds to the A fluid type of the A fluid connected to the A fluid passage, to display on the display of the dialysis fluid preparation the error message indicating malfunction of the dialysis fluid preparation apparatus.

14. The dialysis fluid preparation apparatus according to claim 8, further comprising
a further detection unit of a further concentration measurement means positioned in the A fluid passage or the water feed passage downstream to the connection of the A fluid passage to the water feed passage,
wherein the dialysis fluid preparation apparatus is configured to use as previously set value a value based on the further electric conductivity measured by the further detection means.

* * * * *